US010166410B2

(12) United States Patent
Liu et al.

(10) Patent No.: US 10,166,410 B2
(45) Date of Patent: Jan. 1, 2019

(54) FOCUSED ULTRASOUND GUIDING SYSTEM AND METHOD THEREOF

(71) Applicant: CHANG GUNG UNIVERSITY, Tao-Yuan (TW)

(72) Inventors: Hao-Li Liu, Tao-Yuan (TW); Hong-Chieh Tsai, Guishan Township, Taoyuan County (TW); Yu-Jen Lu, Guishan Township, Taoyuan County (TW); Kuo-Chen Wei, Guishan Township, Taoyuan County (TW)

(73) Assignee: CHANG GUNG UNIVERSITY, Tao-Yuan (TW)

( * ) Notice: Subject to any disclaimer, the term of this patent is extended or adjusted under 35 U.S.C. 154(b) by 924 days.

(21) Appl. No.: 13/779,134

(22) Filed: Feb. 27, 2013

(65) Prior Publication Data

US 2013/0331685 A1 Dec. 12, 2013

(30) Foreign Application Priority Data

Jun. 8, 2012 (CN) .......................... 2012 1 0190164

(51) Int. Cl.
*A61N 7/00* (2006.01)
*A61B 5/055* (2006.01)
(Continued)

(52) U.S. Cl.
CPC .............. *A61N 7/00* (2013.01); *A61B 5/0042* (2013.01); *A61B 5/055* (2013.01); *A61B 5/4836* (2013.01);
(Continued)

(58) Field of Classification Search
CPC ......... A61B 8/00; A61B 90/11; A61B 8/0808; A61B 5/0042; A61B 5/055; A61B 5/4836;
(Continued)

(56) References Cited

U.S. PATENT DOCUMENTS 5,354,314 A * 10/1994 Hardy .................. A61N 5/1031
378/206
5,388,583 A * 2/1995 Ragauskas ............. A61B 5/031
600/438

(Continued)

OTHER PUBLICATIONS

Hynynen, Kullervo, PhD, et al., "Noninvasive MR Imaging-guided Focal Opening of the Blood-Brain Barrier in Rabbits", Radiology, (2001), pp. 640-646.
McDannold, Nathan et al., "MRI-Guided Targeted Blood-Brain Barrier Disruption With Focused Ultrasound: Histological Findings in Rabbits", Ultrasound in Med. & Biol., (2005), pp. 1527-1537.

(Continued)

*Primary Examiner* — Sanjay Cattungal
(74) *Attorney, Agent, or Firm* — Muncy, Geissler, Olds & Lowe, P.C.

(57) ABSTRACT

The present invention discloses a neuronavigation-guided focused ultrasound system and a method for the same, which are used to guide focused ultrasound energy to a target point. The system of the present invention comprises a focused ultrasound device, a neuronavigation system and a fixture. According to an image of an interested region of an individual, a focus point of the focused ultrasound device, and tracking points provided by the neuronavigation system, the neuronavigation system performs a calibration process and establishes a positional relationship between the focus point and the image of the interested region. Thereby, the neuronavigation system can recognize the focus point and guide focused ultrasound to the target point.

16 Claims, 20 Drawing Sheets

(51) Int. Cl.
- *A61B 5/00* (2006.01)
- *A61B 8/08* (2006.01)
- *A61N 7/02* (2006.01)
- *A61B 90/11* (2016.01)
- *A61B 6/03* (2006.01)
- *A61B 6/00* (2006.01)
- *A61B 17/00* (2006.01)
- *A61B 90/50* (2016.01)
- *A61B 90/00* (2016.01)

(52) U.S. Cl.
CPC .............. *A61B 8/0808* (2013.01); *A61B 90/11* (2016.02); *A61N 7/02* (2013.01); *A61B 5/4839* (2013.01); *A61B 6/032* (2013.01); *A61B 6/501* (2013.01); *A61B 90/50* (2016.02); *A61B 2017/00725* (2013.01); *A61B 2090/374* (2016.02); *A61B 2090/3762* (2016.02); *A61N 2007/0021* (2013.01); *F04C 2270/041* (2013.01)

(58) Field of Classification Search
CPC .............. A61B 90/50; A61B 2090/374; A61B 2090/3762; A61B 2017/00725; A61B 5/4839; A61B 6/501; A61B 6/032; A61N 7/00; A61N 7/02; A61N 2007/0021; F04C 2270/041
See application file for complete search history.

(56) References Cited

U.S. PATENT DOCUMENTS

| | | |
|---|---|---|
| 5,752,515 A | 5/1998 | Jolesz et al. |
| 6,351,659 B1 | 2/2002 | Vilsmeier |
| 6,546,277 B1* | 4/2003 | Franck ................... A61B 90/10 600/426 |
| 7,139,601 B2 | 11/2006 | Bucholz et al. |
| 2003/0014016 A1* | 1/2003 | Purdy ........................... 604/174 |
| 2007/0167787 A1* | 7/2007 | Glossop .................. A61B 8/00 600/447 |
| 2008/0200926 A1* | 8/2008 | Verard et al. ................. 606/130 |
| 2009/0112133 A1* | 4/2009 | Deisseroth ............... A61N 7/00 601/3 |
| 2010/0106019 A1* | 4/2010 | Friemel et al. ............... 600/439 |
| 2011/0009734 A1* | 1/2011 | Foley et al. ................... 600/411 |
| 2011/0112394 A1* | 5/2011 | Mishelevich ...... A61N 1/36025 600/411 |
| 2012/0289869 A1* | 11/2012 | Tyler ................................. 601/2 |
| 2013/0055788 A1* | 3/2013 | Amit .............................. 73/1.82 |
| 2013/0237977 A1* | 9/2013 | McCarthy et al. ............. 606/20 |

OTHER PUBLICATIONS

Wei, K.-C. et al., "Neuronavigation-Guided Focused Ultrasound-Induced Blood-Brain Barrier Opening in Swine", 12$^{th}$ International Symposium for Therapeutic Ultrasound, (2012) Preliminary Program Oral Presentation pp. 1-7.

Wei, K.-C et al., Neuronavigation-Guided Focused Ultrasound-Induced Blood-Brain Barrier Opening: A Preliminary Study in Swine, AJNR Am J Neuroradiol (2012) pp. 5-11.

* cited by examiner

FOCUSED ULTRASOUND GUIDING SYSTEM AND METHOD THEREOF

BACKGROUND OF THE INVENTION

Field of the Invention

The present invention relates to a focused ultrasound system, particularly to a neuronavigation-guided focused ultrasound system and a method for the same.

Description of the Related Art

Focused ultrasound (FUS) is highly penetrative to human tissue and able to reach deep within the human body while concentrating most of the ultrasonic energy on a region as small as a grain of rice. Current clinical applications of focused ultrasound include tissue or tumor cauterization, stimulating local or deep-seated cells, regulating local or deep-seated cells, enhancing blood vessel permeability, dissolving thrombi, locally delivering medicine, and disrupting blood brain barrier. Most of the energy of focused ultrasound is concentrated on a focus point. This allows focused ultrasound to destroy deep local tissue non-invasively without damaging the tissue along the path. In addition to the applications mentioned above, focused ultrasound can also be applied to many fields of clinical medicine, such as stimulating local or deep-seated cells, increasing permeability of blood vessels, dissolving thrombi, and locally delivering medicine.

A particular difficulty encountered in application of focused ultrasound is the lack of a fine navigation device for guiding the ultrasound energy to the target easily and precisely.

At present, focused ultrasound is guided by MRI (Magnetic Resonance Imaging), which detects the heat of ultrasound-induced vibration of water molecules to position the focus point, whereby the focus point can be guided to the target region. The technology can provide real-time monitoring in thermal therapy. However, this technology requires integration of all focused ultrasound devices with the MRI system and embedding them in the MRI system. The current MRI-based focused ultrasound guiding system is expensive and hard to design because it requires high-end MRI fabrication technology and corresponding FUS MR-compatibility design.

As mentioned above, MRI can provide real-time monitoring during thermal therapy. However, MRI cannot provide real-time monitoring when focused ultrasound is used to locally enhance the blood-to-brain permeability. Instead, the operator has to inject the imaging contrast agent into the patient once more and undertake MRI scanning again to examine whether the blood-to-brain permeability is enhanced after the treatment with focused ultrasound, which makes MRI-based technology very complicated to employ. No guiding system is clinically available thus far for the application of focused ultrasound to enhance the blood-to-brain permeability. Moreover, real-time feedback control is unlikely to be realized in the current MRI-based focused ultrasound guiding technology.

Furthermore, for a therapy requiring repeated delivery of drugs to the patient, such as multiple chemotherapeutic regimens for a cancer patient, MRI scanning is needed for each repeated cycle of focused ultrasound treatment for drug delivery, which consumes significant time and medical resources.

Therefore, the professionals in the field are eager for a new guiding-positioning technology to be developed that can effectively concentrate focused ultrasound on a target region of a patient.

SUMMARY OF THE INVENTION

The primary objective of the present invention is to provide a focused ultrasound delivery system and method guided by a neuronavigation system for delivering an energy, representing a novel and practical system using a neuronavigation system to guide focused ultrasound and a method for the same.

Another objective of the present invention is to provide a focused ultrasound delivery system and method guided by a neuronavigation system for delivering an energy, which use a neuronavigation system to precisely deliver ultrasound to a target region, and which can apply to enhance the blood-to-brain permeability.

A further objective of the present invention is to provide a focused ultrasound delivery system and method guided by a neuronavigation system for delivering an energy, wherein the focused ultrasound apparatus is neither integrated with an MRI system nor operated in an MRI chamber, so as to increase flexibility of application and reduce the cost of fabrication.

To achieve the abovementioned objectives, the present invention proposes a neuronavigation-guided focused ultrasound system, which guides focused ultrasound energy to a target point, and which comprises a focused ultrasound device, a neuronavigation system, and a fixture. The focused ultrasound device can concentrate ultrasound on a focus point. The neuronavigation system electrically connects with the focused ultrasound device and includes a calibration unit used to establish a positional relationship between the focus point and an interested region of an individual, calibrate coordinates, and recognize the focus point. The fixture is used to fix the interested region of the individual.

In one embodiment, the energy generated by the focused ultrasound device can be applied to cauterization, stimulating local or deep-seated cells, regulating local or deep-seated cells, enhancing blood vessel permeability, dissolving thrombi, locally delivering medicine, and enhancing the blood-to-brain permeability.

The present invention applies to the regions where the neuronavigation system can reach, including the tissues of the central nervous system (such as the brain and the spinal cord) and the tissues wrapped by hard tissues.

The present invention also proposes a focused ultrasound delivery method guided by a neuronavigation system for delivering an energy, which guides focused ultrasound to concentrate on a target point, and which comprises the following steps of:
(1) providing a neuronavigation-guided focused ultrasound system, which comprises a focused ultrasound device, a neuronavigation system, and a fixture;
(2) obtaining an image of a interested region of an individual;
(3) providing a focus point of the focused energy in a space coordinate system;
(4) establishing the positional relationship between the interested region and the focus point;
(5) calibrating the coordinates of the focus point and the interested region to enable the neuronavigation system to recognize the focus point;
(6) guiding the focus point to the target point with the neuronavigation system; and (7) delivering the energy to the target point with the focused ultrasound device.

In one embodiment of the present invention, the method further comprises a step of detecting an echo signal change to monitor the treatment effectiveness in real-time.

Embodiments are described below in detail in conjunction with the attached drawings to illustrate the objectives, technical contents, characteristics and accomplishments of the present invention.

DETAILED DESCRIPTION OF THE INVENTION

The present invention discloses a neuronavigation-guided focused ultrasound system, wherein the neuronavigation system guiding tangible surgical instruments is turned to guide an intangible focused ultrasound energy, and implement a novel and practical operation system.

The present invention is exempted from requiring integration of the focused ultrasound devices with the MRI system and is realized instead via combining the existing neuronavigation system and focused ultrasound devices, thereby improving the flexibility of the operation system. As the present invention does not need to perform a focused ultrasound treatment inside an MRI chamber, the treatment process is simplified.

Below, the present invention is exemplified by an embodiment of using the neuronavigation system to guide focused ultrasound energy on a target region of the brain of a patient to enhance the blood-to-brain permeability. However, the present invention is not limited by the embodiment. The present invention can be applied to any region the neuronavigation system can reach, including the tissues of the central nervous system (such as the brain and the spinal cord) and the tissues wrapped by hard tissues.

Figure 1:
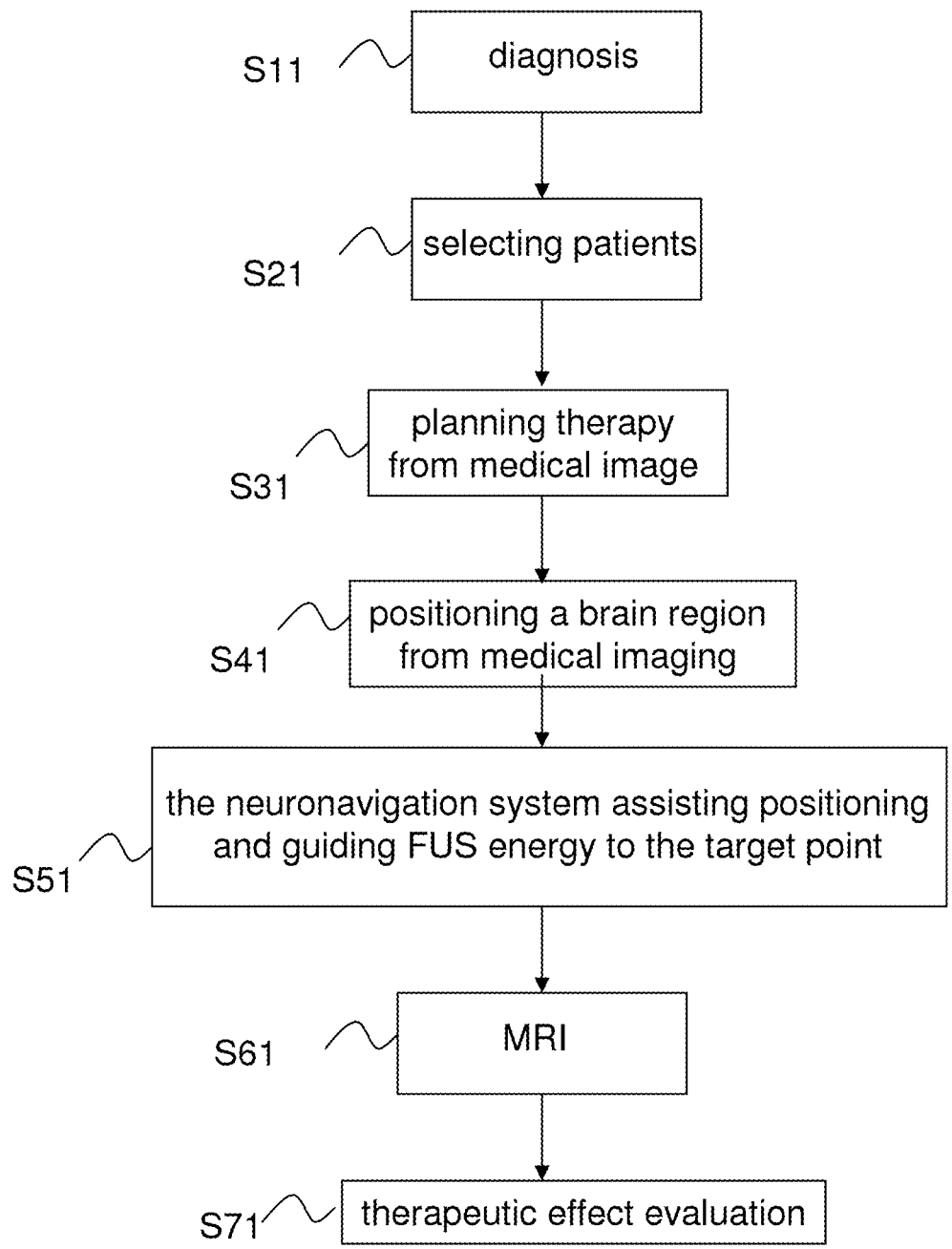
FIG. 1 shows a flowchart of a focused ultrasound treatment implemented by a neuronavigation-guided focused ultrasound system according to one embodiment of the present invention.

Referring to FIG. 1, The focused ultrasound treatment on the brain is used to explain the difference between the prior art and the present invention. The conventional MRI-guided focused ultrasound treatment includes Step S11-Step S41 and Step S61-S71. In Step S11, some patients are diagnosed as having a brain disease. In Step S21, the patients suitable to be treated with focused ultrasound are selected. In Step S31, the therapeutic process for the selected patients is planned. In Step S41, MRI is used to position the region in the patient's brain, and a focused ultrasound treatment is performed on the region. In Step S61, MRI is used again to verify the effect of the focused ultrasound treatment. In Step S71, the effect of therapy is tracked. In some cases, such as the chemotherapy for brain cancer, patients would experience the abovementioned steps once again after each medicine administration. Therefore, multiple cycles of focused ultrasound treatments are needed.

The present invention includes Step S11-Step S51 and Step S71. Unlike the conventional technology, in Step S41, the present invention may use MRI, CT (Computed Tomography), or other methods to position a region in the brain of a patient which is to be treated by focused ultrasound. In Step S51, the present invention uses the neuronavigation system to guide focused ultrasound to the target point to be treated. In Step S51, the present invention can evaluate the effect of focused ultrasound treatment in real time and perform feedback control instantaneously. If multiple cycles of focused ultrasound treatment are required, the present invention does not require MRI to be performed every cycle, but uses the brain images obtained previously and the neuronavigation system to guide focused ultrasound each cycle. After the focused ultrasound treatment, the physician uses MRI to verify the effect of the focused ultrasound treatment. In Step S71, the physician tracks the effect of therapy.

The conventional technology requires integrating the focused ultrasound devices with the MRI system. Further, the conventional technology requires performance of Step S41-Step S61 inside an MRI chamber. Also, for therapy needing multiple cycles of focused ultrasound treatment, MRI must be undertaken in each cycle in the conventional technology, which is very complicated and costly in terms of medical resource. In contrast, the present invention neither integrates the focused ultrasound devices with the MRI system nor undertakes Step S51 inside the MRI chamber. For therapy needing multiple cycles of focused ultrasound treatment, the previously obtained images of patient's interested region are available for neuronavigation system to position the target point and guide focused ultrasound in each cycle in the present invention. Therefore, the present invention eliminates the need for complicated medical device design and operation. From the above description, it is apparent that the present invention is distinct from the conventional technology.

It should be noted that in the present invention the source of images of interested regions of patients is not limited to MRI but may alternatively be from another medical image technology, such as CT. The embodiment in which images of interested regions are sourced from MRI is only to exemplify the present invention, not to limit the scope of the present invention.

Figure 2:
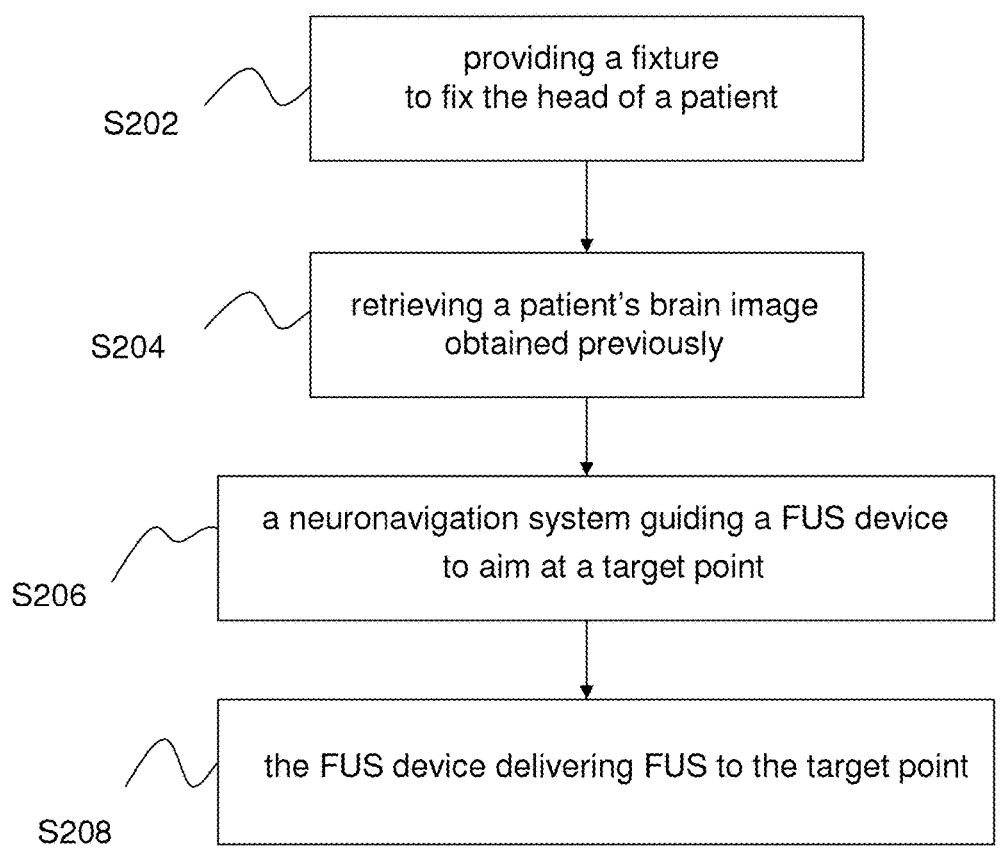
FIG. 2 shows a flowchart of using a neuronavigation system to guide energy delivery of focused ultrasound according to one embodiment of the present invention.

Referring to FIG. 2, showing the flowchart of a neuronavigation-guided focused ultrasound delivery method according to one embodiment of the present invention, the method of the present invention is to guide focused ultrasound to concentrate on a target point in a patient's tissue and comprises Steps S202, S204, S206 and S208.

Figure 3:
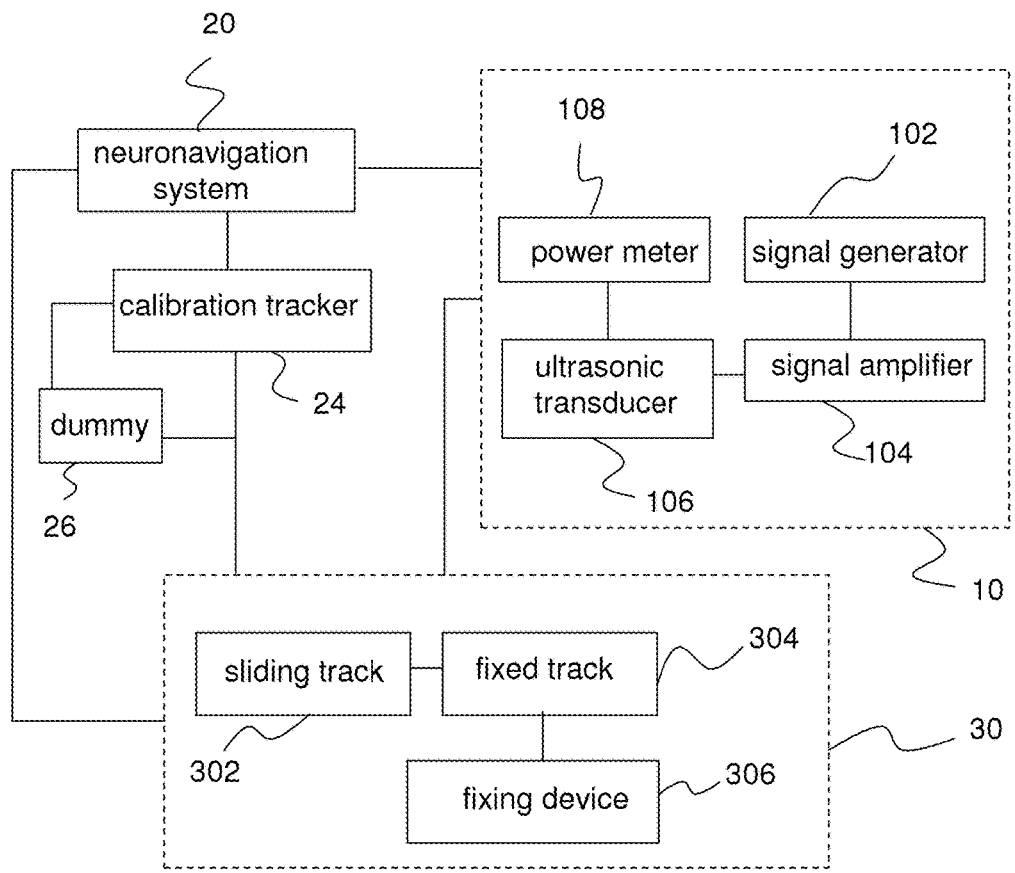
FIG. 3 is a block diagram schematically showing the architecture of a neuronavigation-guided focused ultrasound energy delivery system according to one embodiment of the present invention.

FIG. 3 is a block diagram showing the architecture of neuronavigation-guided focused ultrasound system according to one embodiment of the present invention. FIGS. 4A-4D are diagrams schematically showing that the ultrasonic transducer, which has been calibrated by the neuronavigation system, is mounted on the track to deliver ultrasonic energy.

Figure 4A:
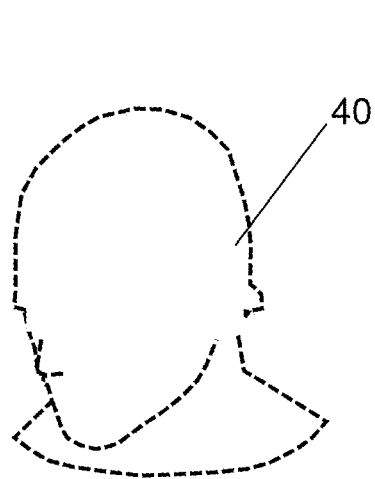
FIGS. 4A-4D schematically show the device and process for fixing the head before a focused ultrasound treatment according to one embodiment of the present invention.
Figure 4B:
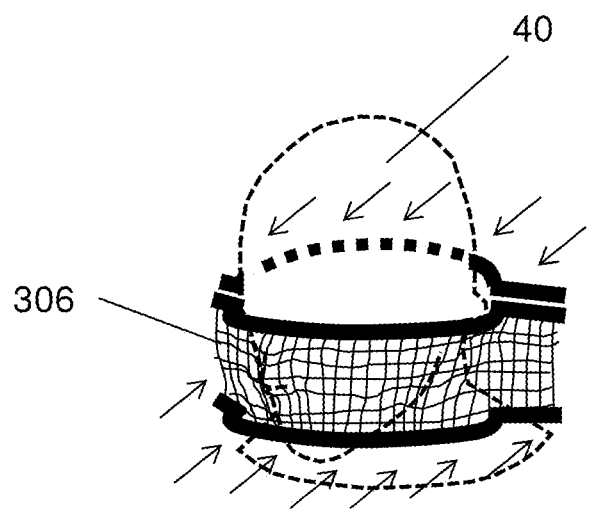

Below is described an embodiment of applying the present invention to a focused ultrasound treatment on the brain. Before the focused ultrasound treatment, a fixing device is used to fix the position of the patient's head. Normally, it is sufficient for the focused ultrasound treatment to use the fixing device to fix the interested region. As shown in FIG. 4A and FIG. 4B, the fixing device 306 may be a thermoplastic mold thermally formed to contact a patient 40. The fixing device 306 can be mounted on and dismounted from the patient 40 repeatedly. The patient 40 is scanned in the image scanning room while wearing the fixing device 306.

Figure 4C:
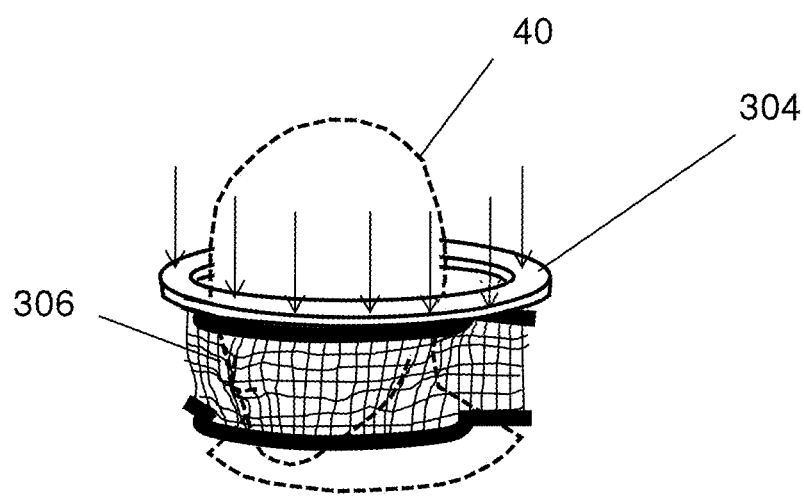

As shown in FIG. 4C, a fixed track 304 is engaged with the fixing device 306. If the patient 40 needs multiple cycles of focused ultrasound treatments, the physician does not need to scan the patient 40 repeatedly. The physician can directly make use of the image information obtained in the first scanning, letting the patient 40 wear the dedicated fixing device 306 to fix the interested region at the same time.

FIGS. 5A-5F are diagrams schematically showing the calibration process according to one embodiment of the present invention. The operation system and the method thereof are described in detail below in FIGS. 2-4 and FIGS. 5A-5F.

In Step S202, a fixture 30 is provided, which may be similar to a stereotactic frame. The fixture 30 is used to fix the head of the patient 40 (as shown in FIGS. 4A-4C) and includes a sliding track 302, a fixed track 304 and a fixing device 306.

In Step S204, the previously obtained brain images of patient 40 (referring to Step S41 in FIG. 1) are retrieved. In Step S206, a neuronavigation system 20 is provided to guide a focused ultrasound device 10 to focus ultrasound energy on a target point.

The neuronavigation system 20 includes a calibration unit providing at least two tracking points P1 and P2. The tracking point P1 provides fixed reference coordinates and is normally arranged at a location whose relative position is invariable with respect to the interested region. It is preferred that the tracking point P1 is arranged on the fixed track 304 of the fixture 30. The ultrasonic transducer 106 of the focused ultrasound device 10 is arranged on the sliding track 302 of the fixture 30. Another tracking point P2 of the neuronavigation system 20 is arranged on the ultrasonic transducer 106 of the focused ultrasound device 10. The present invention performs a calibration process to define the position of the target point according to the tracking points P1 and P2, the patient's brain images obtained in Step S204, and the focus point O of the focused ultrasound device 10.

In Step S208, the focused ultrasound device 10 delivers energy to the defined target point to increase the blood-to-brain permeability of the local tissue at the target point.

Referring to FIG. 3 for one embodiment, the focused ultrasound device 10 electrically connects with the neuronavigation system 20 and includes a signal generator 102, a signal amplifier 104, an ultrasonic transducer 106, and a power meter 108. The signal generator 102 outputs an ultrasonic signal V1. The signal amplifier 104 connects with the signal generator 102 and amplifies the ultrasonic signal V1 to generate focused ultrasound V2. The ultrasonic transducer 106 connects with the signal amplifier 104 and delivers the focused ultrasound V2 to the target point. The power meter 108 connects with the ultrasonic transducer 106 and measures the energy of the focused ultrasound V2.

In one embodiment, the ultrasonic signal V1 may be a sinusoidal signal. The central frequency of the focused ultrasound V2 resonates with the ultrasonic transducer 106.

In one embodiment, the neuronavigation system 20 includes a computer unit and its related software, firmware and memory. The neuronavigation system 20 records the brain images of the patient 40 and provides the tracking points P1 and P2. The neuronavigation system 20 performs the calibration process according to the brain images of the patient 40, the focus point O of the focused ultrasound device 10, and the tracking points P1 and P2. In one embodiment, the tracking point P1 is arranged on the fixed track 304 of the fixture 30, functioning as a reference point having a set of fixed coordinates in space. The tracking point P2 is arranged on a sensing point of the ultrasonic transducer 106.

Figure 5A:
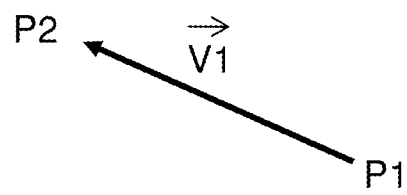
FIGS. 5A and 5B which schematically show how the neuronavigation system recognizes connection between the tracking point P1 and the focus point O according to one embodiment of the present invention.
Figure 5B:
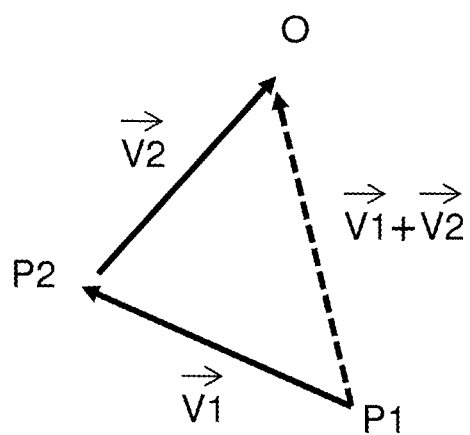

Refer to FIGS. 5A and 5B which schematically show how the neuronavigation system recognizes connection between the tracking point P1 and the focus point O. In FIG. 5A, the neuronavigation system recognizes P1 and P2, calibrates the accuracy thereof, makes a connection between them, and generate a spatial vector $\overline{v1}$ that points from P1 to P2 (the coordinate of $\overline{v1}$ is denoted as (x1,y1,z1)).

In FIG. 5B, the neuronavigation system further recognizes P2 and O, calibrates the accuracy thereof, makes a connection between them, and generates another spatial vector $\overline{v2}$ that points from P2 to O (the coordinate of $\overline{v2}$ is denoted as (x2,y2,z2)).

Once the steps shown in FIGS. 5A and 5B are performed, the neuronavigation system can recognize and make connection between P1 and O by performing the vector sum of $\overline{v1}+\overline{v2}$ (by mathematically obtaining the coordinates of (x1+x2, y1+y2, z1+z2)).

Figure 4D:
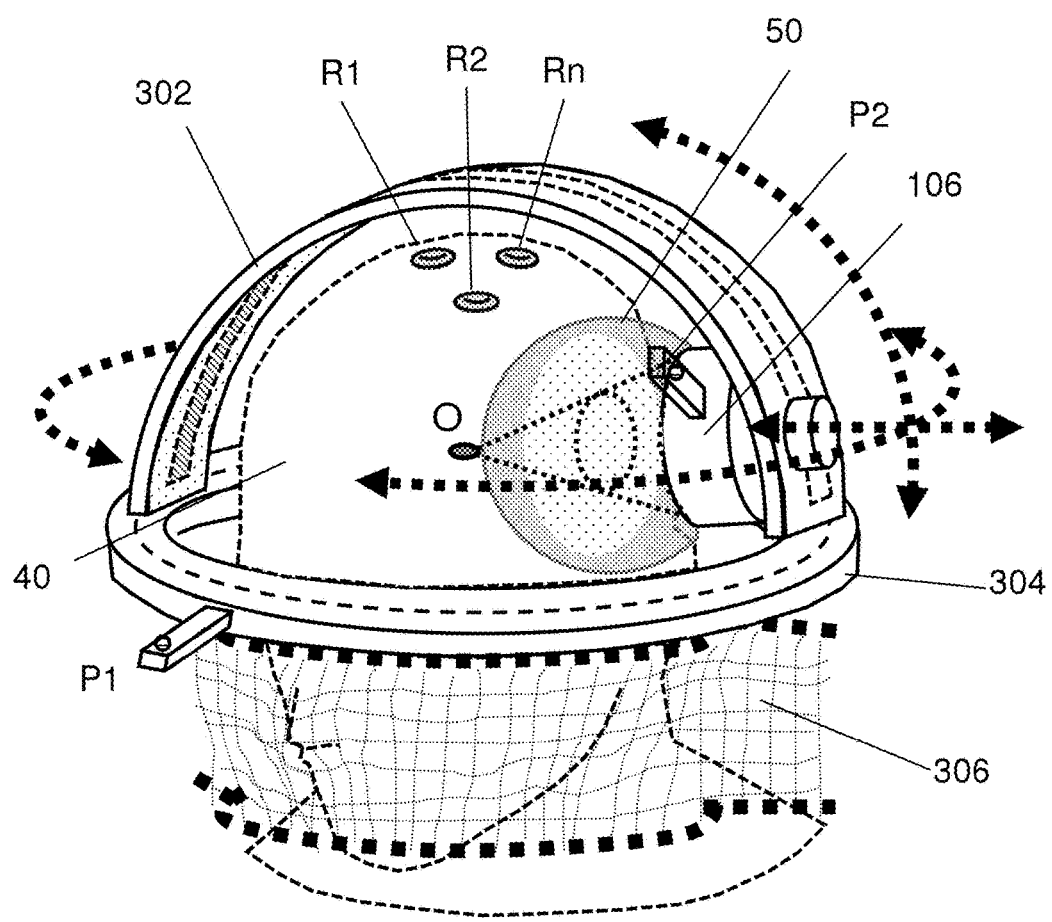

As mentioned above, the fixture 30 includes a sliding track 302 and a fixed track 304. The neuronavigation system 20 uses the tracking point P1 arranged on the fixed track 304 of the fixture 30 and the tracking point P2 to perform the calibration process for defining the target point. The ultrasonic transducer 106 is arranged on the sliding track 302 and slides along the sliding track 302 back and forth, delivering focused ultrasound to the defined focused point O. As shown in FIG. 4D, the sliding track 302 can rotate 360 degrees with respect to a first axis, and the ultrasonic transducer 106 arranged on the sliding track 302 can rotate with respect to a second axis (with maximally 180 degree rotation), which is vertical to the first axis. Thus, the ultrasonic transducer 106 can move to an arbitrary position in the 3D space and deliver focused ultrasound to the target point from an arbitrary position in the 3D space.

The material of the fixing device 306 should be suitable for the imaging system. For example, an MRI system should avoid unsuitable material so that there is no unexpected noise interference with imaging that might cause an erroneous result.

The following describes in detail how to integrate the focused ultrasound device 10 with the neuronavigation system 20 and how the neuronavigation system 20 executes the calibration process.

The focused ultrasound device 10 and the neuronavigation system 20 are two completely different instruments, for which a new calibration process is needed to achieve stable integration there in between.

In the conventional calibration of physical surgical instruments, a calibration tracker 24 (different from the tracking points P1 and P2) is used to assist in calibration. The calibration tracker 24 can allow a neuronavigation system to identify the physical surgical instruments that may be used in surgery through a calibration procedure. The method by which the neuronavigation system calibrates tangible surgical instruments is a conventional technology and will not be described herein. The present invention proposes a novel calibration process to calibrate an intangible ultrasonic focus point O. The novel calibration process proposed by the present invention is described in detail below.

Figure 5C:
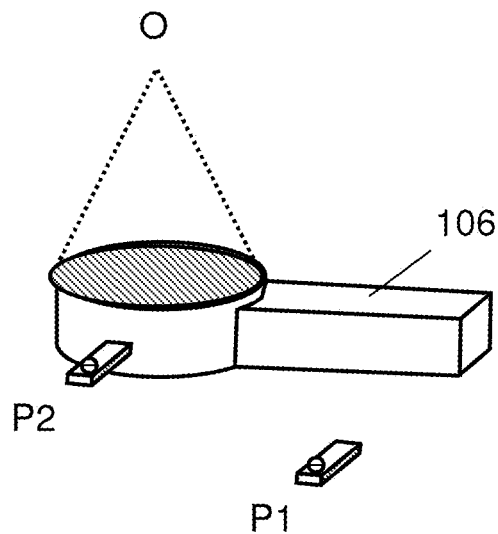
FIG. 5C and FIG. 5D schematically show the focused ultrasound device, the tracking points P1 and P2, the dummy and the reference points in a calibration process according to one embodiment of the present invention.
Figure 5D:
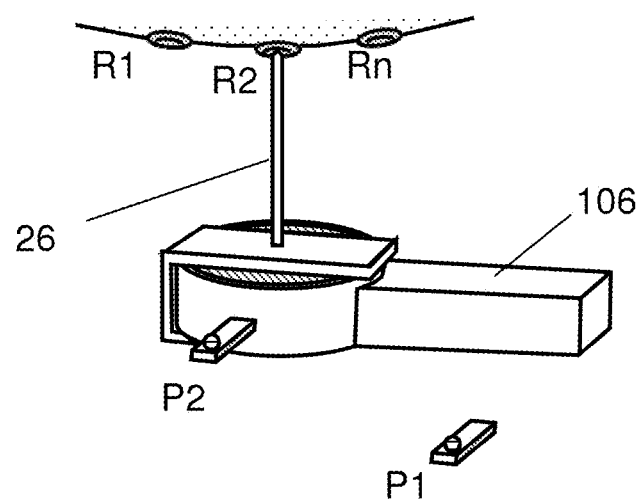
Figure 6:
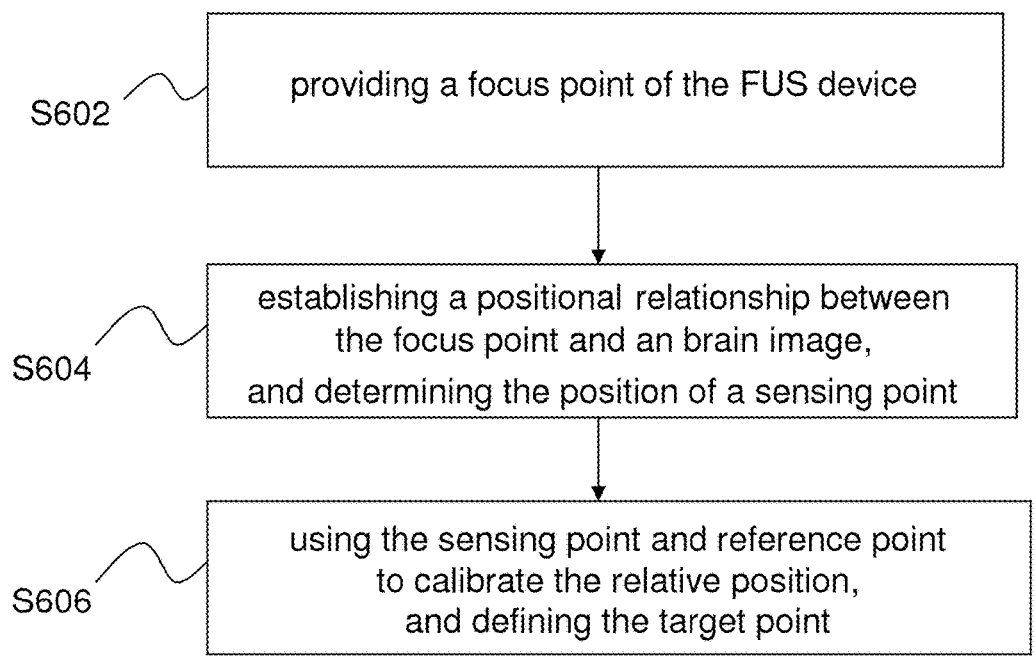
FIG. 6 shows a flowchart of a calibration process according to one embodiment of the present invention.

FIG. 5C and FIG. 5D are diagrams schematically showing a calibration process according to one embodiment of the present invention. Meanwhile, also refer to FIG. 6 which shows the flowchart of a calibration process according to one embodiment of the present invention.

In Step S602, the focus point O of the focused ultrasound device is determined. The focus point O and the complete 3D energy distribution in the acoustic field can be obtained via a precision underwater ultrasonic acoustic field measurement. In order to define the focus point O of the focused ultrasound device, the present invention proposes a dummy 26 of the ultrasonic transducer, which will cooperate with the calibration tracker 24. In one embodiment, the dummy 26 is a T-shape dummy, which is used to assist the calibration tracker 24 to precisely determine the position of the focus point of the focused ultrasound energy in space. The T-shape dummy 26 attaches to ultrasonic transducer 106, and the intangible focus point is transiently replaced by the tangible tip of the T-shape dummy 26, as shown in FIG. 5D.

In Step S604, the dummy 26 is used to point out the position of the focus point O, and an intra-image calibration process is performed. Firstly, the brain images of the patient are input to the neuronavigation system, and several reference points R1, R2, . . . , Rn on the head of the patient are defined, as shown in FIG. 5D. (Since the markers R1 . . . Rn will be attached in the $1^{st}$ MRI, the following calibration process can be proceeded; R1 . . . Rn attachment is a standard neuronavigation guidance calibration procedure). The neuronavigation system records the reference points R1, R2, . . . , Rn and determines the coordinates of the reference points in the brain images. The calibration tracker 24 assists the neuronavigation system to perform coordinate comparison and determine whether the coordinates are within the tolerance. In one embodiment, the sensing point P2 is arranged on the ultrasonic transducer 106 so as to sequentially establish the relationships of the focus point O and the coordinates in the brain images corresponding to the reference points R1, R2, . . . , Rn, thereby establishing the positional relationship between the sensing point P2 and the focus point O in the images.

In Step S606, a calibration process is performed on an image-space transformation. The neuronavigation system begins to search for the position of the sensing point P2 in space; meanwhile, the fixed coordinates of P1 appear on the screen. The neuronavigation system uses the relative positions of the reference point P1 and the sensing point P2 to calibrate the coordinates of P2, referring to the reference points R1, R2, . . . , Rn. Assisted by the calibration tracker 24, the neuronavigation system compares the spatial position and the coordinates in the image to determine whether the spatial position matches the coordinates. At this moment, the neuronavigation can identify the focused point O based on the known spatial relationship between P1 and P2 as well as the spatial relationship between P2 and O. Once the calibration of the focus point of focused ultrasound is completed, the T-shape dummy 26 is taken off. Thus, the neuronavigation system can identify the intangible focus point O and define the target point of focused ultrasound.

Figure 5E:
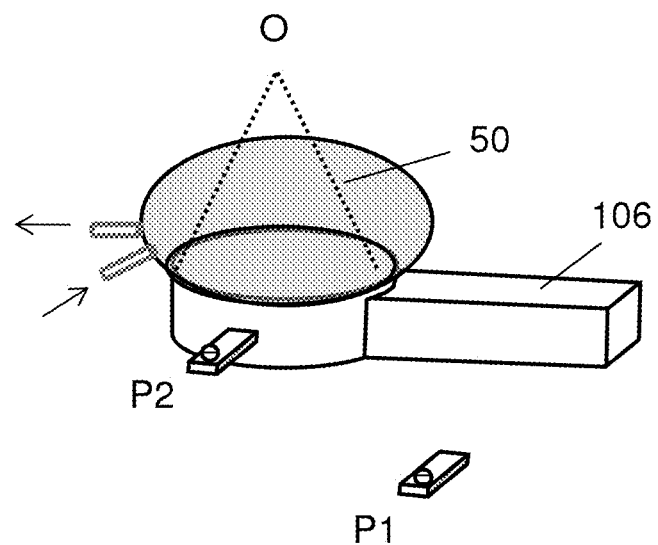
FIG. 5F and FIG. 5F schematically show that a water bag is bound to an ultrasonic transducer and the ultrasonic transducer is mounted on a sliding track after the calibration process according to one embodiment of the present invention.
Figure 5F:
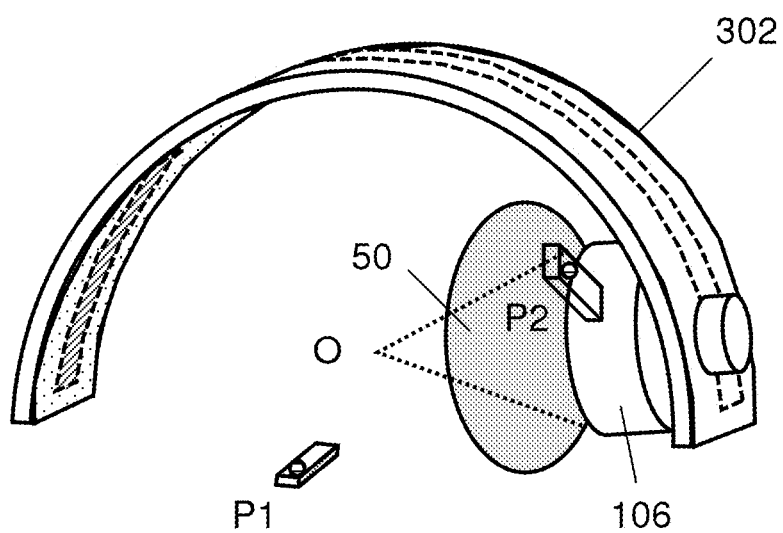

Next, a water bag 50 is bound to the ultrasonic transducer 106 to serve as an ultrasound energy transmission coupling, and the ultrasonic transducer 106 is mounted on the sliding track 302, as shown in FIG. 5E and FIG. 5F. Meanwhile, the neuronavigation system continues to track the focus point O of focused ultrasound. FIG. 4D schematically shows that the ultrasonic transducer mounted on the sliding track undertakes a focused ultrasound treatment. In such a case, the tracking points P1, P2 and the focus point O appear on the screen simultaneously, thereby enabling the physical position of the target point to be precisely located. Then, the focused ultrasound device delivers focused ultrasound energy to the target point.

In conclusion, the present invention proposes a system and method to guide the focused ultrasound to the target point fast, accurately and efficiently. The focus point of focused ultrasound is normally separated from the ultrasonic transducer by a distance of several centimeters to more than 10 centimeters. Further, the focus point is merely the size of a grain of rice. The advantage of focused ultrasound "concentrating ultrasonic energy on a specified target point" cannot be fully realized unless the focused ultrasound is precisely guided by the system and method of the present invention. The present invention integrates the focused ultrasound device and the neuronavigation system and applies to the regions where the neuronavigation system can reach. The present invention can be used to enhance the blood-to-brain permeability to deliver medicine to the brain. The present invention can also be used to locally cauterize deep-seated tissue of the central nervous system, regulate or stimulate local or deep-seated cells, increase permeability of local vessels, dissolve local thrombi, and locally deliver medicine or therapeutic substances into the brain, for example, small-molecule chemotherapeutic agents, therapeutic peptides, monoclonal antibodies, genes, viral vectors, or cells.

Figure 7:
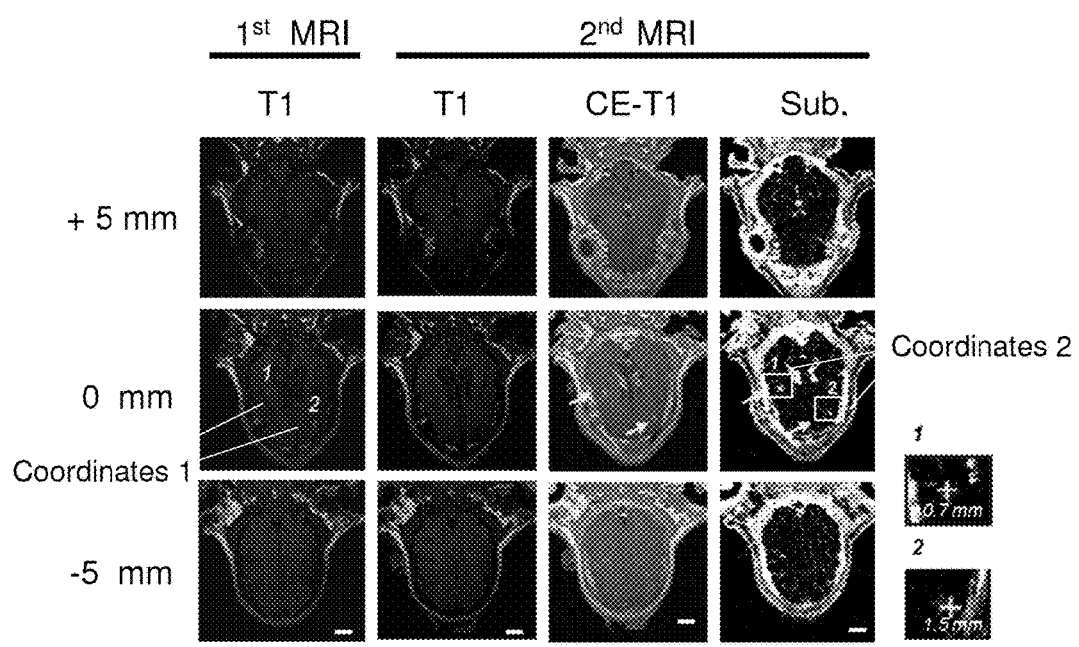
FIG. 7 shows the outcomes of MRI for evaluating the results of the experiment using the neuronavigation system to guide focused ultrasound to enhance the blood-to-brain permeability of an animal according to one embodiment of the present invention.

FIG. 7 shows the outcomes of MRI for evaluating the results of the experiment using the neuronavigation system to guide focused ultrasound to enhance the blood-to-brain permeability of an animal (a young pig) according to one embodiment of the present invention. After performing the $1^{st}$ MRI imaging acquisition, the abovementioned focused point calibration process is performed. Next, focused ultrasound is locally delivered to stimulate the target point. Meanwhile, microbubbles may be injected into the animal to enhance the blood-to-brain permeability. Next, the animal is scanned in the MRI chamber to verify the effect of the focused ultrasound treatment guided by the neuronavigation system. Before the MRI scanning, an MRI imaging contrast agent is injected into the animal. If the permeability of the local vessels is increased, the MRI imaging contrast agent (Gd-DTPA) will enter the brain tissue. Meanwhile, the distance is measured between the target point and the region where the imaging contrast agent leaks into the brain tissue. In FIG. 7, Point 1 and Point 2 of Coordinates 1 in the first column are the target points; Point 1 and Point 2 of Coordinates 2 in the fourth column are the positions where focused ultrasound actually acts. The MR T1-weighted images in the first and second columns are used to detect whether the tested animal is displaced between the first imaging activity (before the focused ultrasound treatment) and the second imaging activity (after the focused ultrasound treatment). The positions where the permeability of vessels increases can be clearly observed in the second column to the fourth column. The arrows indicate the positions of the target points and the positions where the focused ultrasound actually acts. The locally-enlarged views in the lower left of FIG. 7 show that the distances between the target points and the positions where focused ultrasound actually acts are only 1.5 mm and 0.7 mm, respectively. The experimental results show that the present invention has an error very close to that of conventional technology, even though the present invention only uses MRI in a portion of the process. Therefore, the present invention is proved to work effectively.

Figure 8A:
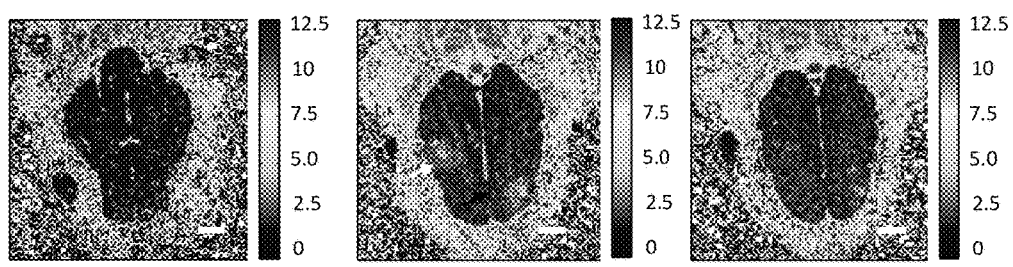
FIG. 8A and FIG. 8B respectively show the MR spin-lattice relaxation rate (R1) analysis and the analysis of contrast agent molecule concentration change at local brain regions according to FIG. 7 after a focused ultrasound treatment.
Figure 8B:
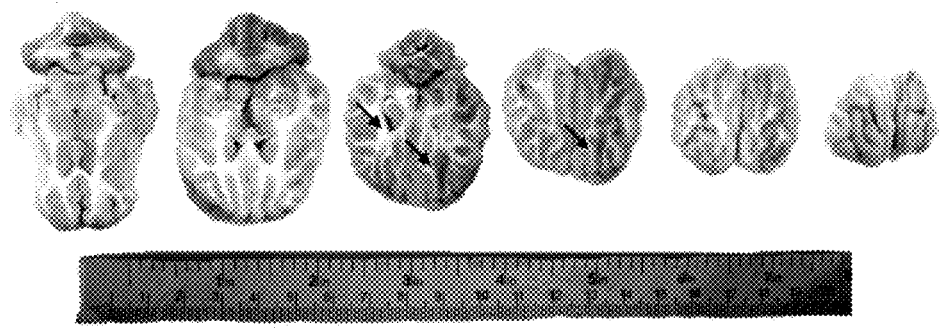

FIG. 8A shows the MR spin-lattice relaxation rate (R1) maps of the arrowed regions having been treated by focused ultrasound in FIG. 7. FIG. 8B shows the analysis images of the regions of the brains according to the identical experimental parameters. FIG. 8A and FIG. 8B further show that the blood-to-brain permeability was increased based on an elevated R1 value increase. Since the MRI contrast agent concentration is linearly correlated with the R1 value, it proves that higher MRI contrast agent concentration was deposited at the target position (in this case it demonstrated at least 100% concentration increase when compared to the unsonicated brain regions). Therefore, the present invention can effectively deliver medicine to a local tissue.

Figure 9A:
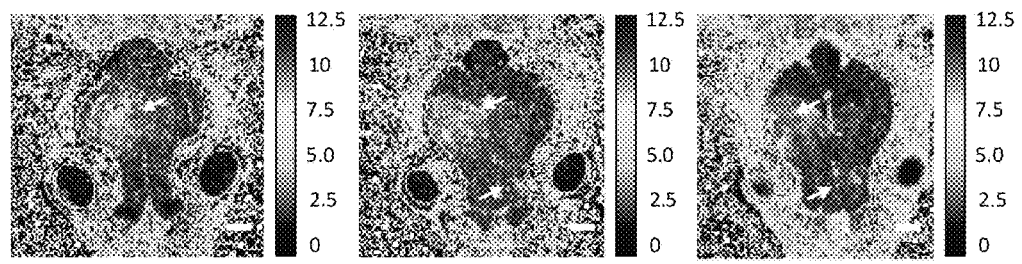
FIG. 9A and FIG. 9B show the results of the experiment using the neuronavigation system to guide a multi-point focused ultrasound treatment to open the blood-brain barrier of animals according to one embodiment of the present invention.
Figure 9B:
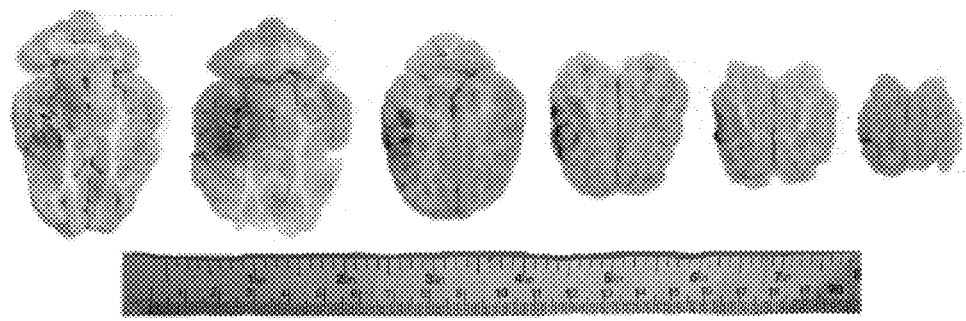

FIG. 9A and FIG. 9B show the results of the experiment using the neuronavigation system to guide a multi-point focused ultrasound treatment to enhance the blood-to-brain permeability of animals according to one embodiment of the present invention, wherein the spacing of each two adjacent focus points is 5 mm, and wherein the focused ultrasound treatments are undertaken 3×3=9 times. FIG. 9A and FIG. 9B show that the area where the blood-to-brain permeability is effectively enhanced by the multi-point focused ultrasound treatment has a diameter of 20 mm, which is much greater than the 4 mm spacing done by the single-point focused ultrasound treatment. Therefore, the multi-point FUS (focused ultrasound) treatment can enhance a large area of blood-to-brain permeability.

Figure 10:
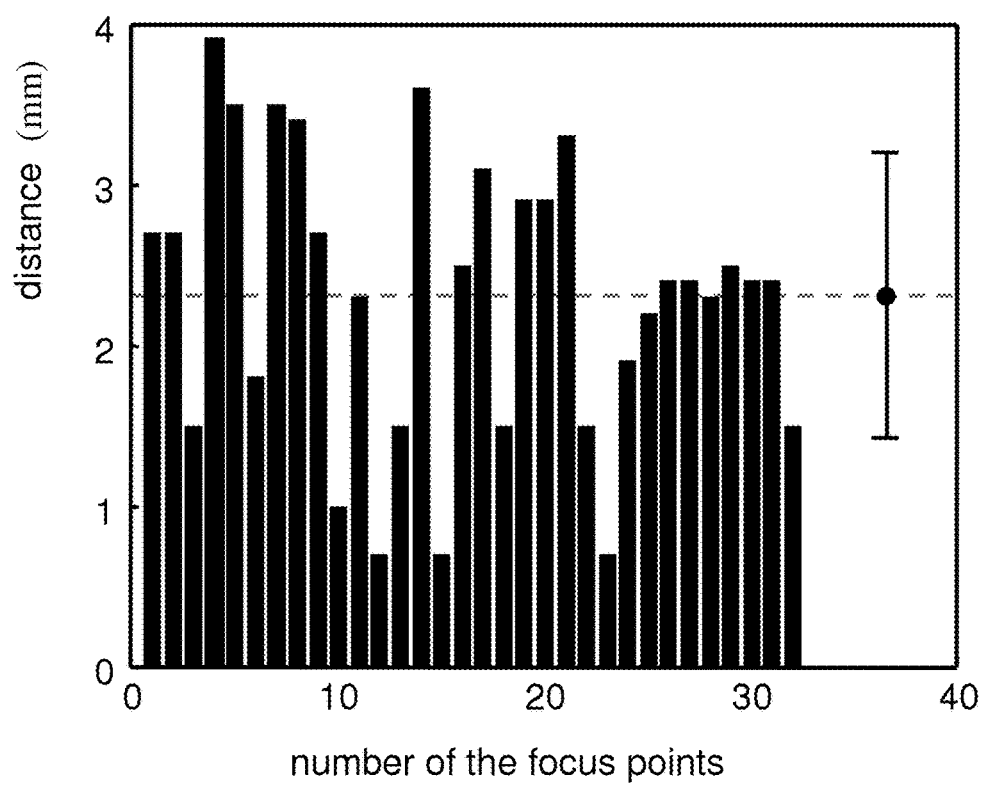
FIG. 10 shows the relationship of the number of the focus points of focused ultrasound (FUS) and the distance between the focus point and the position where FUS actually acts.

FIG. 10 shows the relationship between the number of focus points of FUS and the distance between the focus point and the position where FUS actually acts. FIG. 10 shows that the distance between the focus point and the position where FUS actually acts is only 2.3±0.9 mm. This proves that the present invention is practical and effective.

Figure 11A:
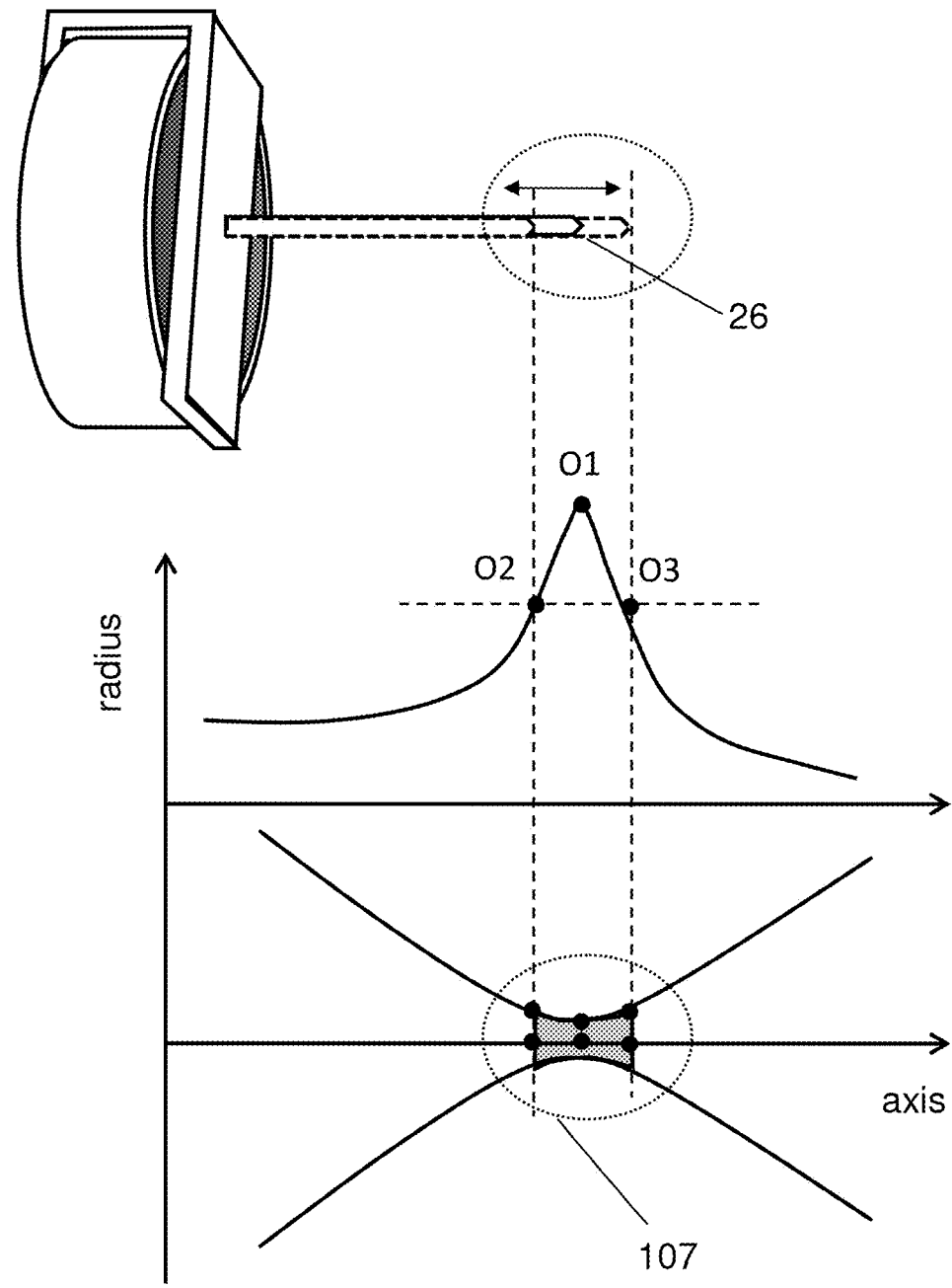
FIGS. 11A-11D schematically show a multi-point FUS positioner to define volumetric FUS energy distribution according to one embodiment of the present invention.
Figure 11B:
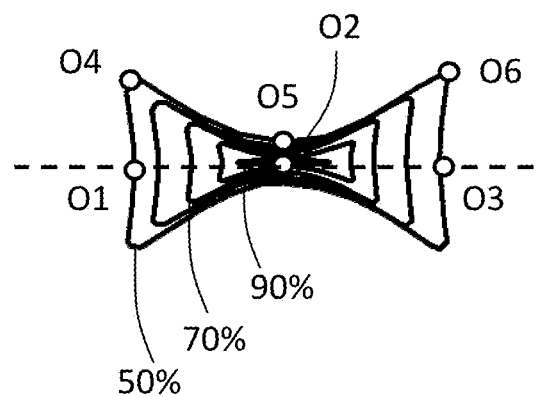
Figure 11C:
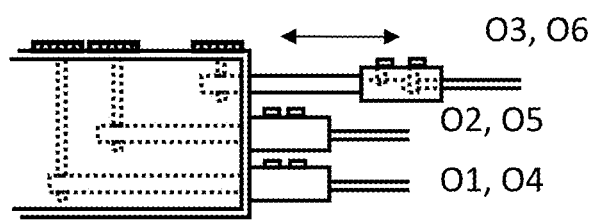
Figure 11D:
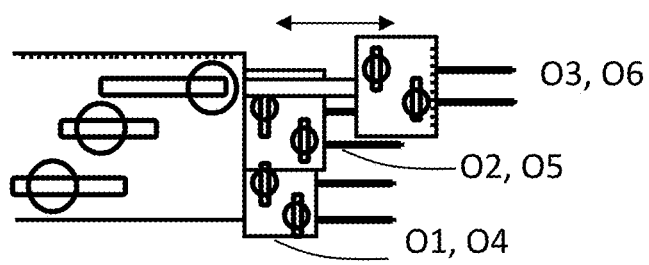

Normally, focused ultrasound is not concentrated on a point but distributed in a 3D space. If focused ultrasound is not guided to an energy point but to an energy space, the guidance will be more precise. Refer to FIGS. 11A-11D for a multi-point FUS positioner according to one embodiment of the present invention, wherein a multi-pin T-shape dummy 26 is used in calibration of a 3D distribution of the focused ultrasound energy (in this example, the present embodiment demonstrated an example to identify the 50% iso-pressure distribution). FIG. 11C and FIG. 11D are respectively a bottom view and a side view of the ultrasonic transducer 106 shown in FIG. 11A. FIG. 11B is a locally-enlarged view of a focused region 107 shown in FIG. 11A. The multi-pin T-shape dummy allows the neuronavigation system to undertake multiple cycles of calibrations in sequence to define the volumetric focused ultrasound energy distribution. The difference between the embodiment and the embodiment of single-point tracking shown in FIGS. 5C-5F resides in the use of a 50% acoustic pressure line to define the volumetric focused ultrasound energy distribution. In FIGS. 11A-11D, O1-O6 respectively represent 6 different locations that all contains 50% focused ultrasound pressure level when compared to the peak pressure one.

Figure 12A:
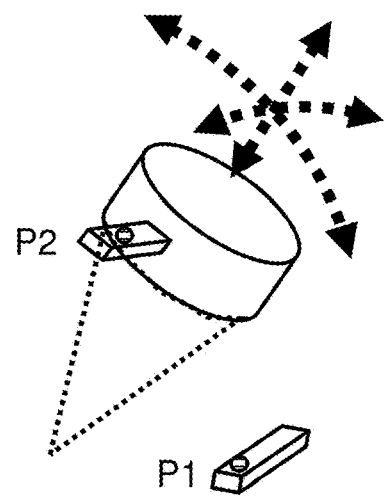
FIGS. 12A-12B schematically show that the focused ultrasound energy guided by the neuronavigation system is manually operated or assisted by a fixation track.
Figure 12B:
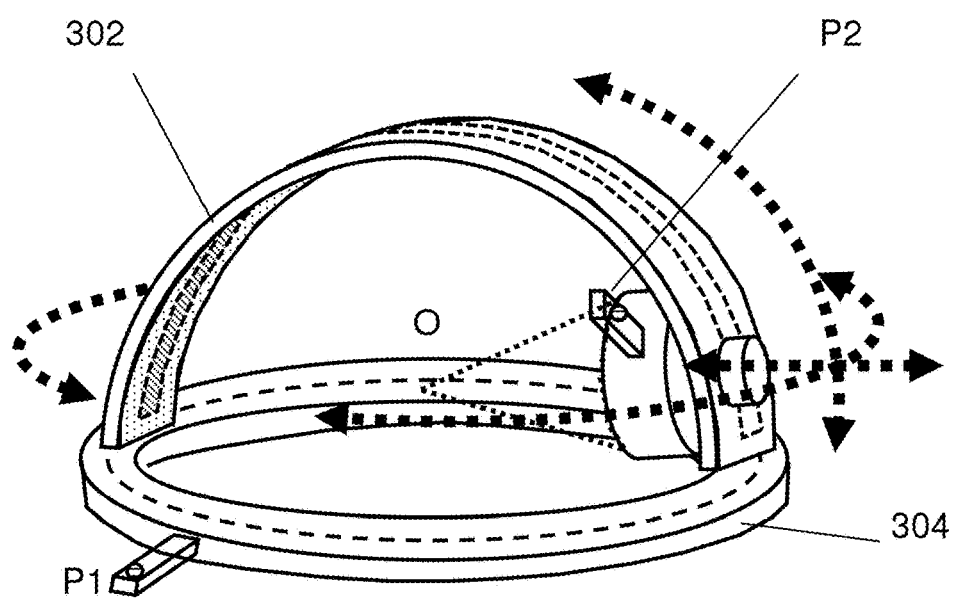
Figure 12C:
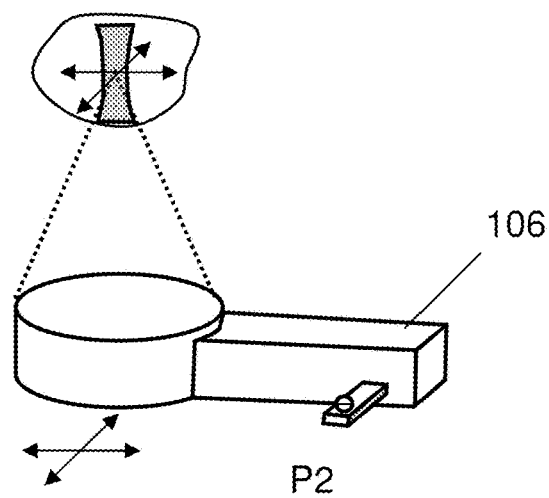
FIGS. 12C-12D show that the focused ultrasound transducer is a spherically focused single element or a multi-element focused ultrasound phased array.
Figure 12D:
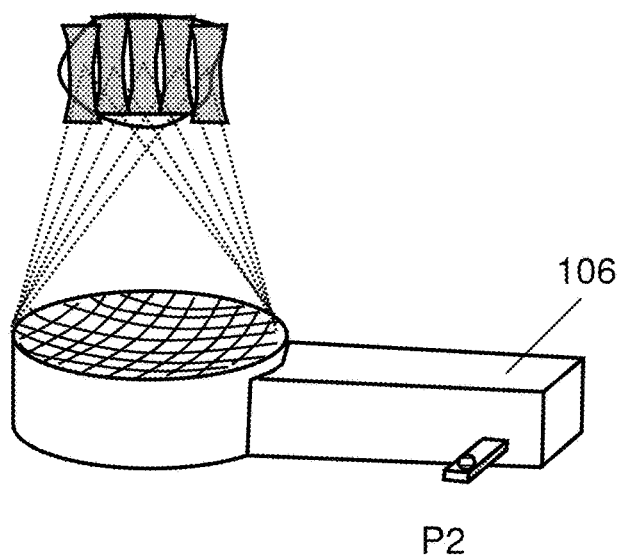

FIG. 12A and FIG. 12B respectively show a manual operation mode and a fixed-track operation mode of multi-point FUS according to one embodiment of the present invention. Either one of the two modes can define a larger 3D focused space, as shown in FIG. 12C and FIG. 12D. FIG. 12C and FIG. 12D demonstrate the real-time control tactics for using a single cycle of FUS or multiple cycles of FUS to implement delivering medicine to the brain tissue according to one embodiment of the present invention, wherein the regions encircled by thick curves are the focused 3D spaces defined by FIG. 11B.

Figure 13A:
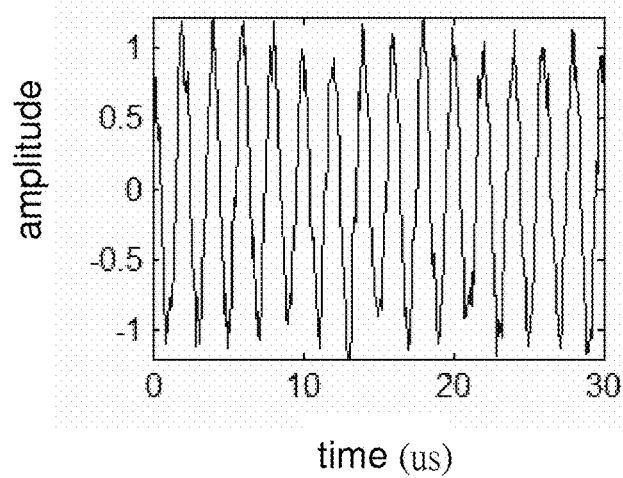
FIG. 13A and FIG. 13B show a of an ultrasonic echo signal and the corresponding spectrum before employing focused ultrasound at the target position according to one embodiment of the present invention.
Figure 13B:
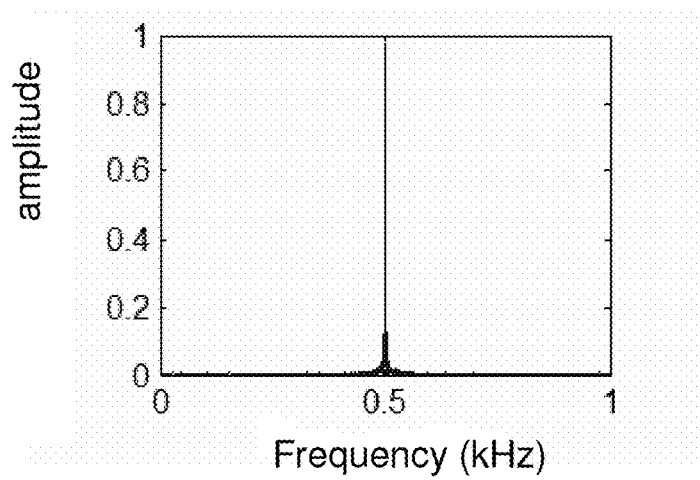
Figure 13C:
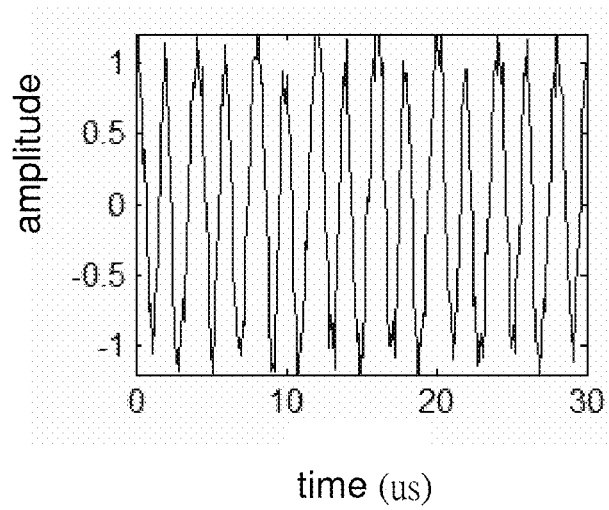
FIG. 13C and FIG. 13D show an typical ultrasonic echo and the corresponding spectrum that contains enhanced subharmonic/ultraharmonic components in using FUS to enhance the blood-to-brain permeability according to one embodiment of the present invention.
Figure 13D:
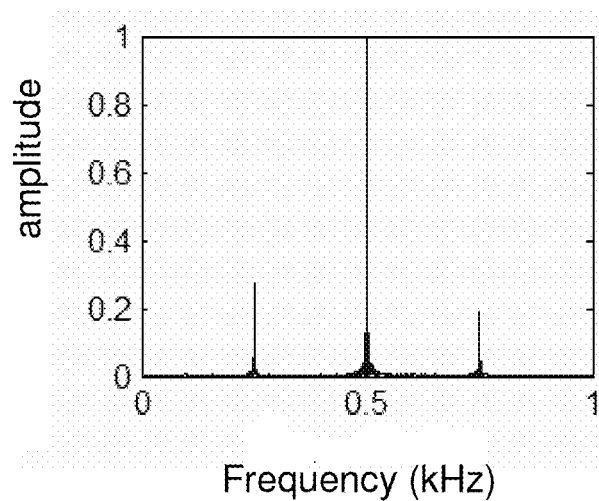

Particular mention should be made of the following: Before the blood-to-brain permeability has been enhanced, the spectrum only contains the base-band frequency, fc (see FIG. 13A and FIG. 13B). If the permeability of the brain vessels increases, a subharmonic or ultraharmonic may accompany the ultrasound echo; if the permeability of the brain vessels does not increase, the subharmonic and ultraharmonic would not appear. Therefore, the present invention determines whether to stop applying ultrasound according to whether the subharmonic or ultraharmonic appears. FIG. 13C and FIG. 13D show a subharmonic and ultraharmonic frequency components, wherein the frequency of the subharmonic is 0.5×fc and 1.5×fc, respectively, and wherein fc is the central frequency of the focused ultrasound.

The present invention detects the characteristic echo to determine whether permeability of local vessels varies in real-time. The subharmonic and superharmonic detection as the feedback loop control index is for use in blood-brain permeability enhancement applications. For other applications, different indexes identified from the received echo signal can be used. For example, for thrombolytic application, one may analyze the Doppler signal change (i.e., frequency shift) received from the echo signal to detect blood-flow/blood velocity recovery.

Figure 14:
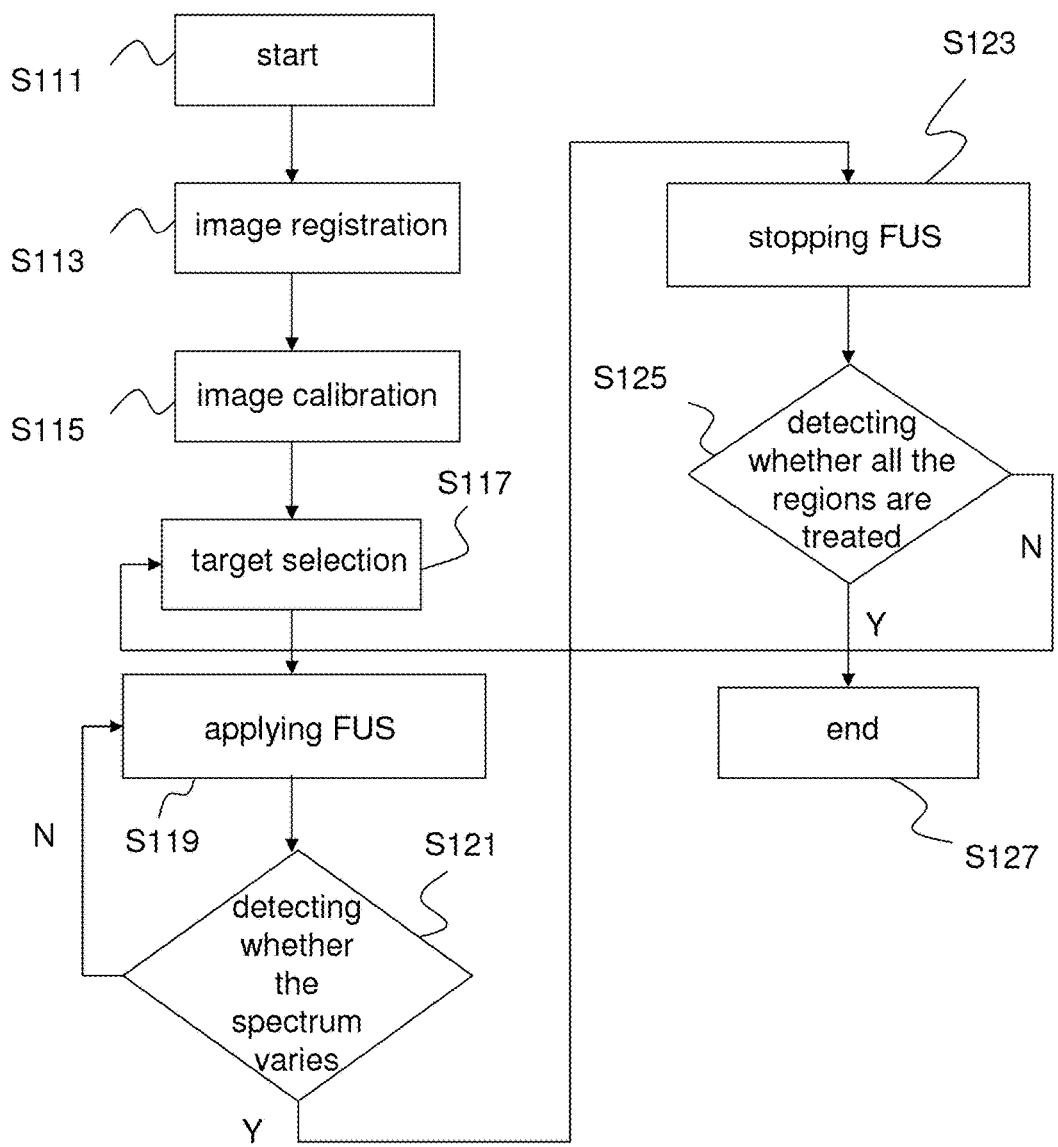
FIG. 14 shows the flowchart of a real-time control tactic for using multi-point FUS to implement delivering medicine to cover a large brain tissue region according to one embodiment of the present invention.

FIG. 14 shows the flowchart of a real-time control tactic for using a single cycle of FUS or multiple cycles of FUS to implement delivering medicine to the brain tissue according to one embodiment of the present invention. As shown in FIG. 14, the multi-point FUS control process comprises Steps S111-S127.

In Steps S111-S119, the brain images obtained previously are retrieved, registration and calibration are performed, the target region is selected and ultrasound is focused on the target region. In Step S121, detection is performed as to whether the spectrum of FUS varies (whether the subharmonic or ultraharmonic appears). If the subharmonic or ultraharmonic appears, application of FUS is ceased (Step S123). If the subharmonic and ultraharmonic do not appear, the process returns to Step S119 and FUS continues to be applied.

After Step S123, the system detects whether all the target regions have been treated. If all the target regions have been treated, the process ends (Step S127). If there is any target region untreated, the process returns to Step S117 and focuses ultrasound on the target region.

It should be noted that in Step S115, the calibration is to define the 3D focused space and use the spectrum variation to determine whether the permeability of blood vessels increases. If the permeability of the blood vessels of the current target region has increased, the treatment turns to the next target region until all the target regions are treated. The calibration process is undertaken according to the calibration points O1-O6 shown in FIG. 11B.

In conclusion, the present invention proposes a focused ultrasound delivery system guided by a neuronavigation system for delivering an energy and a method for the same, which is a novel technology using the neuronavigation system to guide focused ultrasound to the target region.

Eliminating the need to integrate the focused ultrasound device with the MRI system, the present invention is characterized in using the existing neuronavigation system to guide FUS. Therefore, the present invention can reduce equipment cost and increase the flexibility of the operation system.

The embodiments described above are to demonstrate the technical thought and characteristics of the present invention to enable he persons skilled in the art to understand, make, and use the present invention. They are not intended to limit the scope of the present invention. Any equivalent modification or variation according to the spirit of the present invention is to be included within the scope of the present invention.

What is claimed is:

1. An ultrasound system, which guides a focused ultrasound energy to a target point located in a tissue of a central nervous system, comprising:
a focused ultrasound device generating a focus point and delivering said energy to said target point which is a tissue wrapped by a hard tissue, and said target point is located in an interested region of an individual;
a first tracking point, a second tracking point and a computer unit, wherein said first tracking point provides fixed reference coordinates and is arranged at a location whose relative position to said interested region of said individual is invariable, and wherein said second tracking point is arranged on an ultrasonic transducer of said focused ultrasound device, and said computer unit retrieves an image of said interested region of said individual, and said image of said interested region of said individual is a previously obtained image obtained with an MRI (Magnetic Resonance Imaging) technology or a CT (Computed Tomography) technology;
reference points on said interested region with spatial positions, and wherein said computer unit records said reference points on said interested region to determine coordinates of said reference points in said image of said interested region;
a calibration tracker connecting with said computer unit;
a dummy arranged on said ultrasonic transducer, wherein said dummy includes a tip pointing out a spatial position of said focus point, and said tip of said dummy, said second tracking point and said first tracking point are tracked by said calibration tracker and said computer unit to search said spatial position of said, focus point and said computer unit compares said spatial positions of said first tracking point, said second tracking point and said reference points with said coordinates of said first tracking point, said second tracking point and said reference points in said image of said interested region to establish the positional relationship between said first tracking point, said second tracking point and said reference points in said image of said interested region, whereby said spatial position of said focus point corresponds to coordinates of said focus point in said image of said interested region based on known positional relationship between said second tracking point and said focus point; and
a fixture fixing said interested region of said individual.

2. The ultrasound system according to claim 1, wherein said focused ultrasound device further comprises
a signal generator generating an ultrasonic signal; and
a signal amplifier electrically connecting with said signal generator, electrically connecting with said ultrasonic transducer and amplifying said ultrasonic signal into said focused ultrasound; and
said ultrasonic transducer delivers said focused ultrasound to said target point, wherein a central frequency of said focused ultrasound resonates with said ultrasonic transducer.

3. The ultrasound system according to claim 2, wherein said focused ultrasound device further includes a power meter electrically connecting with said ultrasonic transducer and measuring power of said focused ultrasound.

4. The ultrasound system according to claim 2, wherein said ultrasonic signal is a sinusoidal signal.

5. The ultrasound system according to claim 1, wherein said fixture comprises a sliding track and a fixed track, and wherein an ultrasonic transducer of said focused ultrasound device is arranged on said sliding track.

6. The ultrasound system according to claim 5, wherein said fixture further comprises a fixing device, and wherein said fixing device is worn by said individual and fixes said interested region of said individual in retrieving said image of said interested region of said individual.

7. The ultrasound system according to claim 6, wherein said fixing device is a thermoplastic mold.

8. The ultrasound system according to claim 1, wherein said fixture comprises a sliding track and a fixed track, and wherein said first tracking point is arranged on said fixed track, and wherein said second tracking point is arranged on said sliding track.

9. The ultrasound system according to claim 1, wherein said focused ultrasound is applied to cauterization, stimulating local or deep-seated cells, regulating local or deep-seated cells, enhancing blood vessel permeability, dissolving thrombi, and locally delivering medicine.

10. The ultrasound system according to claim 1, wherein said focused ultrasound is applied to enhance blood-to-brain permeability.

11. The ultrasound system according to claim 1, wherein said focused ultrasound device is a multi-point focused ultrasound device.

12. A focused ultrasound energy delivery method for delivering an energy, which guides a focused ultrasound energy to a target point located in a tissue of a central nervous system, comprising steps of:

providing a ultrasound system comprising a focused ultrasound device, a fixture, a dummy and a calibration tracker, wherein said ultrasound system further includes a first tracking point, a second tracking point and a computer unit, and wherein said first tracking point provides fixed reference coordinates and is arranged at a location whose relative position to an interested region of an individual is invariable, and wherein said second tracking point is arranged on an ultrasonic transducer of said focused ultrasound device, and wherein said dummy is arranged on said ultrasonic transducer, wherein said dummy includes a tip pointing out a spatial position of said focus point, and wherein said calibration tracker connects with said computer unit, wherein said focused ultrasound device generates said energy, and wherein said ultrasound system guides said energy to said target point which is a tissue wrapped by a hard tissue, and said target point is located in said interested region, and wherein said fixture fixes said interested region;

using said computer unit to retrieve an image of said interested region of said individual, wherein said image is obtained with an MRI (Magnetic Resonance Imaging) technology or a CT (Computed Tomography) technology;

providing reference points on said interested region, wherein said reference points are located at spatial positions using said computer unit to record said reference points on said interested region to determine coordinates of said reference points in said image of said interested region, and using said calibration tracker and said computer unit to track said tip of said dummy, said second tracking point and said first tracking point to search said spatial position of said focus point;

using said computer unit to compare said spatial positions of said first tracking point, said second tracking and said reference points with said coordinates of said first tracking point, said second tracking and said reference points in said image of said interested region to establish the positional relationship between said first tracking point, said second tracking point and said reference points in said image of said interested region, whereby said spatial position of said focus point corresponds to coordinates of said focus point in said image of said interested region based on known positional relationship between said second tracking point and said focus point;

guiding said focus point to said target point with said ultrasound system; and delivering said energy to said target point with said focused ultrasound device.

13. The method according to claim 12, wherein said focused ultrasound energy is applied to cauterization, stimulating local or deep-seated cells, regulating local or deep-seated cells, enhancing blood vessel permeability, dissolving thrombi, and locally delivering medicine.

14. The method according to claim 12, wherein said focused ultrasound is applied to enhancing blood-to-brain permeability.

15. The method according to claim 12, further comprising a step of stopping output of said focused ultrasound energy when a subharmonic or a ultraharmonic accompanies an ultrasonic echo.

16. The method according to claim 12, wherein said focused ultrasound device is a multi-point focused ultrasound device.

* * * * *